United States Patent
Shangguan et al.

(10) Patent No.: US 9,463,450 B1
(45) Date of Patent: Oct. 11, 2016

(54) POLYMERIC ACID CATALYSIS

(71) Applicants: Ning Shangguan, Cherry Hill, NJ (US); Andrew Feiring, Wilmington, DE (US); Ashokkumar B. Shenvi, Wilmington, DE (US)

(72) Inventors: Ning Shangguan, Cherry Hill, NJ (US); Andrew Feiring, Wilmington, DE (US); Ashokkumar B. Shenvi, Wilmington, DE (US)

(73) Assignee: Compact Membrane Systems, Inc., Newport, DE (US)

( * ) Notice: Subject to any disclaimer, the term of this patent is extended or adjusted under 35 U.S.C. 154(b) by 0 days.

(21) Appl. No.: 15/078,065

(22) Filed: Mar. 23, 2016

Related U.S. Application Data

(60) Provisional application No. 62/138,130, filed on Mar. 25, 2015.

(51) Int. Cl.
| | | |
|---|---|---|
| *C07D 493/00* | (2006.01) | |
| *B01J 31/06* | (2006.01) | |
| *C07D 493/04* | (2006.01) | |
| *C07C 213/00* | (2006.01) | |

(52) U.S. Cl.
CPC .............. *B01J 31/06* (2013.01); *C07C 213/00* (2013.01); *C07D 493/04* (2013.01)

(58) Field of Classification Search
CPC ........................................................ B01J 31/06
USPC ........................................................ 549/464
See application file for complete search history.

(56) References Cited

U.S. PATENT DOCUMENTS

| | | |
|---|---|---|
| 4,935,477 A | 6/1990 | Squire |
| 7,220,508 B2 | 5/2007 | Watakabe et al. |
| 2010/0314038 A1 | 12/2010 | Tanuma |
| 2013/0245219 A1 | 9/2013 | Perry et al. |

OTHER PUBLICATIONS

Harmer, Mark A., et al., Solid Acid Catalysis Using Ion-exchange Resins, Applied Catalysis A: General 221 (2001) 45-62.

*Primary Examiner* — Nizal Chandrakumar
(74) *Attorney, Agent, or Firm* — Jeffrey C. Lew

(57) ABSTRACT

A highly fluorinated polymer is very useful as an acid catalyst. The highly fluorinated polymer has at least two repeating unit types that are the polymerized derivatives of a perfluorinated cyclic or cyclizable compound and a highly fluorinated vinyl ether compound having a sulfur containing functional group. The polymer can be formed by radical copolymerization of the fluorinated monomers with the sulfur-containing functional group in sulfonyl fluoride form ($-SO_2F$) that is subsequently converted to sulfonic acid form ($-SO_3H$). The highly fluorinated polymer can be used to advantage in a solution comprising an aprotic, polar organic solvent that has a dielectric constant of at least 15 and preferably is free of hydroxyl functional groups. Suitable solvents are those in which the polymer is soluble to at least 1 wt %. Hydroxyl group-containing protic, polar organic solvents are less preferred. The highly fluorinated polymer can be an effective heterogeneous catalysts when used in form of solid, fine particles insolubly suspended in or in contact with a fluid reaction mass.

15 Claims, No Drawings

POLYMERIC ACID CATALYSIS

This invention was made with government support under grant numbers NIH 8R43GM103416-02 and NIH 5R44GM077717-03 awarded by the National Institutes of Health. The government has certain rights in this invention.

FIELD OF THE INVENTION

This invention relates to using a highly fluorinated, sulfonic acid group-substituted polymer to catalyze chemical reactions that require or benefit from strong acid catalysts. It also relates to a solution containing a highly fluorinated, sulfonic acid group-substituted polymer dissolved preferably in a polar, aprotic, high dielectric, organic solvent, or water, and a method of using the solution. More specifically, it relates to a solution of a copolymer of a perfluorinated vinyl ether monomer having a pendant sulfonic acid functional group and a cyclic or cyclizable perfluorinated monomer dissolved in a polar, aprotic organic solvent having a dielectric constant of at least 15 or water.

BACKGROUND OF THE INVENTION

Many chemical reactions, such as the synthesis of organic compounds for pharmaceutical applications and the reformation of petroleum products, are catalyzed by strong acids. Representative industrially important types of acid catalyzed organic reactions include Friedel-Crafts alkylation and acylation of aromatic compounds, Schiff base formation from ketones and primary amines, acetal and ketal syntheses, and nitration of aromatic compounds. In the petroleum industry, the alkylation of olefins such as isobutene, for example, is a critical process for production of gasoline. Common mineral acids, such as sulfuric, nitric, hydrochloric, hydrofluoric and phosphoric acids, have long been employed in these chemical reactions, but have well recognized drawbacks. For example, these deficiencies include the need to employ wasteful and expensive rigorous supplemental separation processes because the final product often must be scrupulously free of the acid or its salts. Also, shipping, handling and storage of industrial scale quantities of mineral acids present safety, environmental and security threats that require costly and productivity inhibiting countermeasures. Furthermore, some of these mineral acids, such as sulfuric and nitric acid, can oxidize reactants to form undesirable by-products. Due to these very serious shortcomings, there has been much interest in developing effective replacements for strong mineral acid catalysts.

Some commercially interesting polymeric strong acids are identified by the formula (1) in which n and m are mole fractions of the respective component in the polymer and x is an integer typically in the range of 0-3. These include compounds such as Nafion®-H and Aquivion® PFSA perfluoroalkanesulfonic acid resins that are heterogeneous in reaction media and thus can simply separate from product. Nafion®-H is a copolymer of tetrafluoroethylene ("TFE") and a perfluorinated vinyl ether with pendant perfluoroalkylsulfonic acid group as shown in formula (1) and in which x=1. Aquivion® is a copolymer of TFE and a perfluorinated vinyl ether with the pendant perfluoroalkylsulfonic acid group shown in formula (1) in which x=0.

(1)

Also available are inorganic solid acids such as zeolites which can be employed as heterogeneous acid catalysts but are prone to fouling.

While heterogeneous catalysts offer to facilitate separation, there are no known significant commercial applications using Nafion® copolymer as an acid catalyst. This may be attributable to low activity relative to traditional, liquid strong acids. Reduced activity results from the low surface area of Nafion® particles and the polymer's inability to swell in most solvents. These factors render most of the acid moiety sites inaccessible to the reactants. Entrapping Nafion®-H within silica gel pores increases the surface area and has been attempted to increase activity. However, plugging of the pores is a common feature of most solid, heterogeneous acid catalysts and can significantly diminish activity.

Acid catalysts based on porous, sulfonated crosslinked polystyrene resins are in common use. See Harmer 2001, Applied Catalysis A: General 221, 45-62. These polymers lack the thermal and chemical stability of the perfluoropolymers and have an acid strength several orders of magnitude less than perfluoroalkylsulfonic acids. They also are subject to loss of activity due to pore plugging.

Non-polymeric, highly fluorinated acid catalysts, such as trifluoromethanesulfonic ("triflic") acid and perfluorooctanesulfonic acid are known as "super acids" because they are orders of magnitude stronger acids than sulfuric acid. Table 1 compares triflic acid strength to sulfuric and acetic acids. Thus, these super acids can be more effective homogeneous catalysts than mineral acids, and can catalyze transformations that standard mineral acids cannot accomplish. Although small molecule perfluorinated acids also have high thermal and chemical stability and are not active oxidizing agents, they do have significant disadvantages. For example, triflic acid is a toxic liquid with boiling point of 162° C. It can cause blindness on eye contact and severe burns on the skin. Longer chain non-polymeric perfluorosulfonic acids, such as perfluorooctane sulfonic acid, are toxic and highly persistent in the environment such that they are readily taken up by and are enduring in living organisms. These characteristics have led to regulations or bans on their use. Consequently, there remains a need for acid catalysts that can dissolve in reaction media for efficient utilization, have stable, superacid strength, can be readily separated from the reaction medium, and are more environmentally benign than traditional strong acid catalysts.

TABLE 1

| Acid | Formula | pKa* |
|---|---|---|
| trifluoromethanesulfonic ("triflic") acid | $CF_3SO_3H$ | −14 |
| sulfuric acid | $H_2SO_4$ | −3.0 |
| acetic acid | $H_3COOH$ | 4.8 |

*acid strength inversely proportional to pKa value

Watakabe et al., U.S. Pat. No. 7,220,508 and Squire, U.S. Pat. No. 4,935,477 disclose copolymers from perfluorinated cyclic monomer, perfluoro-2,2-dimethyl-1,3-dioxole ("PDD"), and a perfluorinated vinyl ether, "SEFVE" (see Table 2, below). In sulfonic acid form, this polymer can be dissolved or well dispersed in organic solvents having hydroxyl groups. Solubility in other organic solvents is not disclosed. Perry et al., US Patent Application 2013/0245219 disclose copolymers of PDD and other cyclic fluorinated monomers with perfluorinated vinyl ethers of formula $CF_2=CFO[CF_2]_nSO_2X$ wherein n is 2, 3, 4 or 5 and X is F, Cl, OH or OM wherein M is a monovalent cation. The use of solutions of these perfluorinated polymers for acid catalysis is not disclosed.

SUMMARY OF THE INVENTION

A highly fluorinated polymer is very useful as an acid catalyst. The highly fluorinated polymer includes two repeating unit types that are the polymerized derivatives of a perfluorinated cyclic or cyclizable compound and a highly fluorinated vinyl ether compound having a sulfur containing functional group. The polymer can be formed by radical copolymerization of the fluorinated monomers with the sulfur-containing functional group in sulfonyl fluoride form (—SO$_2$F) that is subsequently converted to sulfonic acid form (—SO$_3$H). The highly fluorinated polymer can be used to advantage in a solution comprising an aprotic, polar organic solvent that has a dielectric constant of at least 15 and preferably is free of hydroxyl functional groups. Suitable solvents are those in which the polymer is soluble to at least about 1 wt %. Hydroxyl group-containing protic, polar organic solvents are less preferred. The highly fluorinated polymer can be an effective heterogeneous catalysts when used in form of solid, fine particles suspended in or in contact with a fluid reaction mass.

The invention thus provides a solution comprising a highly flourinated polymeric acid dissolved in a polar, aprotic solvent having a dielectric constant of at least about 15, in which the highly fluorinated polymeric acid consists essentially of a copolymer according to the formula -[A]$_m$-[B]$_n$- in which A and B are present preferably in random order and m and n are the respective mole fractions of repeating units in the copolymer, in which A is a polymerized derivative of a perfluorinated cyclic or cyclizable compound, in which B is a polymerized derivative of a fluorinated vinyl ether compound containing a pendant sulfonic acid moiety, and in which the solvent is capable of dissolving the highly fluorinated polymeric acid to at least 1 wt % of the solution.

The invention also provides a solution comprising a highly flourinated polymeric acid dissolved in water, in which the highly fluorinated polymeric acid consists essentially of a copolymer according to the formula -[A]$_m$-[B]$_n$- in which A and B are present in random order and m and n are the respective mole fractions of repeating units in the copolymer, in which A is a polymerized derivative of a perfluorinated cyclic or cyclizable compound, and in which B is a polymerized derivative of a fluorinated vinyl ether compound containing a pendant sulfonic acid moiety.

There is further provided a method of increasing acidity of a substance comprising the steps of (A) providing a highly fluorinated polymeric acid consisting essentially of a copolymer according to the formula -[A]$_m$-[B]$_n$- in which A and B are present in random order and m and n are the respective mole fractions of repeating units in the copolymer, in which A is a polymerized derivative of a perfluorinated cyclic or cyclizable compound, and in which B is a polymerized derivative of a fluorinated vinyl ether compound containing a pendant sulfonic acid moiety, and (B) intimately mixing the substance and the highly fluorinated polymeric acid for a duration effective to increase acidity of the substance.

Still further the invention provides a method of increasing the acidity of a substance comprising the steps of (A) providing a highly fluorinated polymeric acid consisting essentially of a copolymer according to the formula -[A]$_m$-[B]$_n$- in which A and B are present in random order and m and n are the respective more fractions of repeating units in the copolymer, in which A is a polymerized derivative of a perfluorinated cyclic or cyclizable compound, and in which B is a polymerized derivative of a fluorinated vinyl ether compound containing a pendant sulfonic acid moiety, and (B) intimately mixing the substance and an acid solution of the highly fluorinated polymeric acid for a duration effective to increase acidity of the substance, in which the acid solution comprises the highly fluorinated polymeric acid dissolved in a solvent of either (i) a polar, aprotic solvent having a dielectric constant of at least about 15 or (ii) a hydroxyl-containing solvent such as water or an alcohol.

DETAILED DESCRIPTION OF THE INVENTION

A glossary of abbreviations used in this disclosure is presented in Table 2.

TABLE 2

| Term | Meaning |
|---|---|
| PDD | perfluoro-2,2-dimethyl-1,3-dioxole |
| POESF | perfluoro(3-oxapent-4-ene)sulfonyl fluoride CF$_2$=CFOCF$_2$CF$_2$SO$_2$F |
| SEFVE | CF$_2$=CFOCF$_2$CF(CF$_3$)OCF$_2$CF$_2$SO$_2$F |
| SEFVE-H | CF$_2$=CFOCF$_2$CF(CF$_3$)OCF$_2$CF$_2$SO$_3$H |

The term "fluid" as used herein means a liquid or a gas.

The polymeric acid comprises at least two types of repeating units "A" and "B" with an overall composition -[A]$_m$-[B]$_n$- in which A and B are present preferably in random order and m and n are the respective mole fractions of repeating units in the polymer. A is a polymerized derivative of a perfluorinated cyclic or cyclizable organic compound. B is a polymerized derivative of a fluorinated vinyl ether compound containing a pendant sulfonic acid moiety and has a structure shown in formula (2),

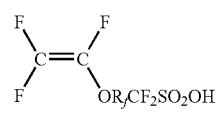

(2)

in which the R$_f$ group is a linear or branched, perfluoroalkyl group containing 1 to 10 carbon atoms and optionally substituted by one or more ether oxygen atoms. In describing the chemical compounds from which the repeating units are derived, the terms "compound" and "monomer" are used interchangeably herein.

It is preferred to copolymerize the cyclic monomer with the fluorinated vinyl ether with the latter in its sulfonyl fluoride form (—SO$_2$F), that is, with F in place of the OH group. After polymerization, the sulfonyl fluoride group is converted to its acid form by techniques well known in the art. For example, the sulfonyl fluoride form polymer can be treated with a strong base such as potassium hydroxide in a mixture of water and alcohol followed by acidification by treatment with an excess of strong acid such as nitric acid. Representative examples of the highly fluorinated vinyl ether compound containing sulfonyl fluoride suitable for polymerization according to this invention include SEFVE, POESF and CF$_2$=CFOCF$_2$CF$_2$CF$_2$SO$_2$F. SEFVE is preferred.

Perfluorinated cyclic repeating unit A has the chemical structure shown in formula (3)

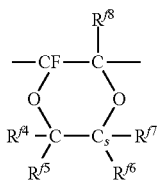

(3)

in which s is 0 or 1, each of $R^{f4}$, $R^{f5}$, $R^{f6}$ and $R^{f7}$ which may be the same or different, is a fluorine atom or a $C_{1-5}$ perfluoroalkyl group, and $R^{f8}$ is a fluorine atom, a $C_{1-5}$ perfluoroalkyl group or a $C_{1-5}$ perfluoroalkoxy group, provided that $R^{f4}$ and $R^{f5}$ may be connected to form a spiro ring when s=0.

A preferred embodiment of cyclic repeating unit A has the chemical structure shown in formula (4) in which $Rf^{16}$ and $Rf^{17}$ each independently is a fluorine atom or a trifluoromethyl group

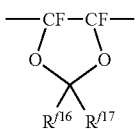

(4)

Representative examples of the perfluorinated cyclic or cyclizable organic compound are perfluoro-2,2-dimethyl-1,3-dioxole ("PDD"). perfluoro-2-methylene-4-methyl-1,3-dioxolane ("PMD"), perfluoro (alkenyl vinylether) ("PFVE"), and 2,2,4-trifluoro-5 trifluoromethoxy-1,3 dioxole ("TFMD"). PDD is preferred.

The cyclizable repeating unit has structure that can be transformed to achieve the cyclic structure of formulae (3) or (4).

The proportion of repeating units A to repeating units B in the polymer chain, (i.e., m:n ratio) for the highly fluorinated polymeric acid can vary widely. Preferably the mole fraction in the polymer of repeating units B is at least about 0.1, more preferably at least about 0.2 and most preferably at least about 0.4. It is recognized in the art that the highly fluorinated vinyl ether compounds copolymerize readily, but can homopolymerize only with difficulty. Therefore the mole fraction of repeat units B should be at most about 0.5.

The acid compound according to this invention is of macromolecular size. Preferably the polymeric acid has a number average molecular weight of about 10,000 to about 1,000,000.

The polymeric acid can optionally include additional comonomers other than compounds that polymerize to type A or B repeating units. Additional comonomers preferably are halogenated hydrocarbons and more preferably fluorinated hydrocarbons. Representative examples of additional comonomers are tetrafluoroethylene, trifluoroethylene, chlorotrifluoroethylene, vinyl fluoride and vinylidene fluoride. The perfluorinated cyclic or cyclizable compounds can homopolymerize as well as copolymerize. When additional comonomers are not present, the mole fraction of repeating units A should be complementary to the mole fraction of repeating units B, (i.e. m and n total to 1.0) When additional comonomers are present, the mole fraction of repeat units A should be at least about 0.3. The ratio of m to n controls the equivalent weight of the resulting acid polymer, that is, the number of grams of polymer affording one mole of acid catalyst. The equivalent weight is readily determined by titration of a carefully weighted amount of the polymer with a standard alkali solution.

A preferred highly fluorinated polymeric acid according to this invention is shown in formula (5) in which the repeating unit "A" is derived from PDD and y is zero or one.

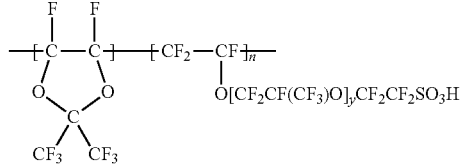

(5)

The highly fluorinated polymeric acid is solid at and above room temperature. Accordingly, it can be a very effective heterogeneous catalyst for reactions taking place in fluid reaction media in which the polymeric acid is not soluble. The polymeric acid can be simply filtered from the reaction mass to provide a substantially, and normally, completely, catalyst-free product.

In another aspect of this invention, the polymeric acid catalyst can be present in solution of a suitable solvent. Preferred solvents are those in which the highly fluorinated polymeric acid is soluble to at least about 1 wt %. In practice of acid catalysis concentration of the highly fluorinated polymeric acid is selected as most effective for each particular reaction system, and can be less than 1 wt %. Concentration as low as about 0.1 wt % polymeric acid solution can be effective. Preferred solvents for dissolving the highly fluorinated polymer acid are aprotic, polar organic solvents, that is, solvents with a dielectric constant of 15 or greater and lacking hydroxyl groups. Representative examples of such solvents include dimethylsulfoxide, dimethylformamide, dimethylacetamide and sulfolane. Solvents containing hydroxyl groups such as alcohols and water may also dissolve the highly fluorinated polymeric acid. Such solvents are less preferred because hydroxyl functionality of the solvent exerts a leveling effect on acid strength which attenuates potency below the full superacid strength.

Results of solubility tests in selected solvents of the preferred polymer of formula (5) in which y is one are presented in Table 3. The polymeric acid with an equivalent weight of about 1000 readily dissolves in hot (80° C.) water and remains soluble when cooled to room temperature. The polymeric acid with an equivalent weight of 1500 also readily dissolves in hot water, but precipitates nearly quantitatively when cooled to room temperature.

TABLE 3

| Solvent | Dielectric Constant | Solubility* at room temperature |
|---|---|---|
| 2H, 3H-Perfluoropentane | | I |
| Heptane | 1.92 | I |
| Toluene | 2.3 | I |
| 1,2-Dichloroethane | 10.42 | I |
| Methylene chloride | 9.1 | I |
| Chloroform | 4.81 | I |
| Dioxane | 2.25 | I |
| Tetrahydrofuran | 7.5 | I |
| Dimethylformamide | 38 | S |
| Dimethylsulfoxide | 46.7 | S |
| Dimethylacetamide | 37.8 | S |

TABLE 3-continued

| Solvent | Dielectric Constant | Solubility* at room temperature |
|---|---|---|
| N-Methylpyrrolidinone | 32 | S |
| Acetonitrile | 37.5 | S |
| Sulfolane | 43.3 | S |
| Ethanol | 24.6 | S |
| Trifluoroethanol | 8.55 | S |
| Trifluoroacetic acid | 8.55 | P |
| Water | 80 | D |

*I = insoluble, S = soluble, P = partially soluble, D = solubility dependent upon equivalent weight.

The highly fluorinated polymeric acid of this invention advantageously provides extensive versatility and thus can be used effectively in the many diverse reaction types known in the art that employ or are facilitated by an acid catalyst. Optimum techniques for deploying the polymeric acid can be different for different reaction systems. In some cases, a homogeneous solution of the highly fluorinated polymeric acid dissolved in a polar, aprotic solvent is preferred. In other cases, for example, where very complete or simplified removal of the acid catalyst from the reaction mass or product is called for, it can be advantageous to conduct heterogeneous catalysis using solid highly fluorinated polymeric acid in contact with the reactants. In still other situations such as when less than superacid catalytical strength is sufficient and a more environmentally benign solvent system is desired, the highly fluorinated polymeric acid can be provided to beneficial effect dissolved in a polar solvent containing hydroxy groups, such as water or alcohols. The particular technique for using the highly fluorinated polymeric acid catalyst can be readily determined on a case-by-case basis by one of ordinary skilled in the art without undue experimentation.

EXAMPLES

This invention is now illustrated by examples of certain representative embodiments thereof, wherein all parts, proportions and percentages are by weight unless otherwise indicated. All units of weight and measure not originally obtained in SI units have been converted to SI units.

Example 1

Synthesis of a Highly Fluorinated Polymeric Acid

Into a glass pressure tube were placed 4.88 g PDD, 17.84 g SEFVE, 5 mL 2,3-dihydrodecafluoropentane (Vertrel® XF specialty fluid, DuPont Wilmington, Del.), and 1 mL initiator solution of hexafluoropropylene oxide (HFPO) dimer peroxide in Vertrel® XF. HFPO dimer peroxide was made from reaction of $CF_3CF_2CF_2OCF(CF_3)CFO$ with basic hydrogen peroxide. The tube was cooled to −78° C. in a dry ice/isopropanol bath, evacuated and filled with nitrogen 3 times. The glass tube was sealed and allowed to warm to room temperature in a water bath. The reaction mixture was agitated by shaking overnight. The tube was opened to ambient air and 20 mL acetone was added into the mixture. After stirring for 15 minutes, the liquid was decanted and 20 mL fresh acetone was added. After stirring for 15 minutes, the liquid was again decanted and the solid residue was transferred to a watch glass. Drying in an oven at 100° C. overnight yielded 6.3 g of white, solid PDD/SEFVE copolymer product.

The PDD/SEFVE copolymer was hydrolyzed with KOH dissolved in a water/ethanol mixed solvent solution, filtered from solution, and then immersed in an aqueous nitric acid solution, drained and re-immersed in aqueous nitric acid to convert to the acid form of the polymer. The acid form polymer was then filtered and rinsed with deionized water and dried under vacuum to obtain poly(PDD/SEFVE-H) copolymer.

Example 2

Solubility of Poly(PDD/SEFVE-H) in Selected Solvents

A 0.21 g sample of the polymer prepared in Example 1 was added to a small glass vial. Solvent (4.0 mL) was added. The vial was capped and allowed to stand for several hours at room temperature. Visual inspection determined whether the polymer had dissolved in the given solvent. The procedure was repeated for each of the solvents listed in Table 3 where results are presented. The result "soluble" indicates that no solid polymer remained in the vial.

Example 3

Solution Catalysis by Poly(PDD/SEFVE-H)

The highly fluorinated polymeric acid prepared in Example 1 was used for the acid catalyzed conversion of sorbitol to isosorbide, as follows. A mixture of 0.5 g of sorbitol, 0.1 g of the polymeric acid catalyst and 5 mL sulfolane was heated to 120° C. giving a homogeneous solution. After 20 hr, the solution was cooled to room temperature and diluted with 5 mL of water. An aliquot of this solution was spotted on a thin layer chromatography TLC plate and dried under vacuum for 2 hr. The TLC plate was also spotted with a solution of isosorbide and the plate was developed using a 9:1 mixture of ethanol to isopropanol. The TLC plate showed complete conversion of the sorbitol to isosorbide. A control experiment preformed in the absence of the acid catalyst showed no isosorbide formation.

Example 4

Heterogeneous Catalysis by Poly(PDD/SEFVE-H)

A magnetically stirred solution of 4-methoxyacetanilide (2 mmol.) in 20 mL of dichloroethane under nitrogen was treated with 70% aqueous nitric acid (2 mmol. 0.127 mL). About 50 mL of samples were withdrawn at various times and diluted with about 0.5 mL of dichloromethane and treated with 0.5 mL of 0.5 M sodium bicarbonate solution. A 50 mL sample of the organic layer was diluted to 1 mL with ethanol and analyzed for extent of conversion using high performance liquid chromatography (HPLC). The conversion yield was calculated using a calibration factor determined from HPLC analysis of a 1:1 mixture of the starting material and commercially purchased product 4-methoxy-2-nitroacetanilide (Sigma-Aldrich Corp., St. Louis, Mo.).

The foregoing procedure was repeated with the addition of 0.1 g acid catalyst powder of this invention as prepared in Example 1. The acid catalyst powder dramatically improved reaction. Absent the solid highly fluorinated polymeric acid catalyst, 60% conversion to product occurred after more than 4 hr. In contrast, in the presence of the solid highly fluorinated polymeric acid catalyst, 60% conversion was achieved in 1.0 hour.

Example 5

Synthesis of a Highly Fluorinated Polymeric Acid

To a reaction vessel cooled in an ice bath and purged with argon gas for 5 minutes was added 2.0 g PDD, 5 mL Vertrel XF, 9.2 g POESF (Synquest Laboratories, Alachua, Fla.) and 0.4 mL HFPO dimer peroxide solution in Vertrel XF (0.12M). The reaction vessel was sealed and the mixture was allowed warm to room temperature by placing in a water bath. After stirring overnight, an additional 2.0 g PDD and 0.4 mL HFPO dimer peroxide solution was added into the vessel and the contained mixture was stirred for an additional overnight time. Acetone (30 mL) was added to the mixture and the resulting precipitate was filtered. The collected solid was dried in oven at 100° C. for 3 hours to give 4.88 g white powder.

A 0.8 g sample of the above copolymer powder was treated with 0.3 g KOH in refluxing ethanol/water (40/10 mL) overnight. After cooling to room temperature, 20 mL of 10% HCl solution was added and the mixture was heated to 90° C. to evaporate most of the ethanol. The solid was filtered and washed twice with 20 mL of 10% HCl solution (10 minutes each time). The copolymer was washed with 30 mL distilled water 2 times and then dried in a 100° C. oven for 3 hours to give 0.70 g polymeric acid. This product was found to be soluble in dimethylformamide.

Although specific forms of the invention have been selected in the preceding disclosure for illustration in specific terms for the purpose of describing these forms of the invention fully and amply for one of average skill in the pertinent art, it should be understood that various substitutions and modifications which bring about substantially equivalent or superior results and/or performance are deemed to be within the scope of the following claims. The entire disclosures of U.S. patents and patent applications named in this disclosure are hereby incorporated by reference herein.

What is claimed is:

1. A method of increasing acidity comprising the steps of
   (A) providing a substance to be highly acidified
   (B) providing a fluorinated polymeric acid formed by copolymerizing monomers comprising (i) a perfluorinated cyclic monomer and, (ii) a fluorinated vinyl ether monomer that contains a pendant sulfonic acid moiety, and
   (C) intimately mixing the substance to be highly acidified with the fluorinated polymeric acid for a duration effective to increase acidity of the substance to be highly acidified,
   in which the perfluorinated cyclic monomer forms in the fluorinated polymeric acid a repeating unit of the following formula

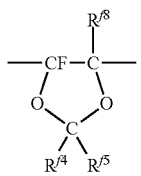

in which $R^{f4}$ and $R^{f5}$ are each independently a fluorine atom or a $C_{1-5}$ perfluoroalkyl group, and $R^{f8}$ is a fluorine atom, a $C_{1-5}$ perfluoroalkyl group or a $C_{1-5}$ perfluoroalkoxy group.

2. The method of claim 1 in which the repeating unit formed by the perfluorinated cyclic monomer has the following formula in which $R^{f16}$ and $R^{f17}$ each independently is a fluorine atom or a trifluoromethyl group, and

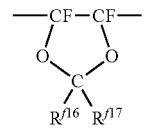

in which the fluorinated vinyl ether monomer forms in the fluorinated polymeric acid a repeating unit formed by the fluorinated vinyl ether monomer of the following formula

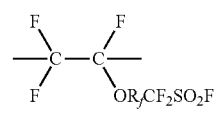

in which the $R_f$ group is a linear or branched, perfluoroalkyl group containing 1 to 10 carbon atoms, and optionally substituted by one or more ether oxygen atoms.

3. The method of claim 2 in which the fluorinated polymeric acid has the following formula wherein y is zero or one, and in which m and n are the respective mole fractions of the repeating units in the fluorinated polymeric acid of the perfluorinated cyclic monomer and the fluorinated vinyl ether monomer

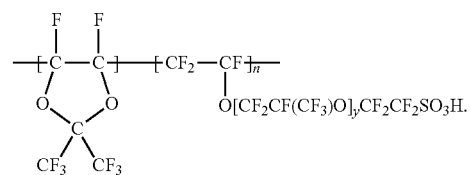

4. The method of claim 1 in which during the intimately mixing step, the substance to be highly acidified is a fluid and the fluorinated polymeric acid is present in a solid state of matter.

5. The method of claim 4 in which the fluid is a liquid, the fluorinated polymeric acid is present as fine particles, and the intimately mixing step comprises dispersing the fine particles substantially uniformly in the liquid.

6. The method of claim 4 in which the substance comprises reactants of an acid-catalyzed chemical reaction mass.

7. The method of claim 1 which further comprises dissolving the fluorinated polymeric acid to at least about 1 wt % in a solvent to form an acid solution, and intimately mixing the substance to be highly acidified with the acid solution.

8. The method of claim 7 in which the solvent is polar, aprotic and has a dielectric constant of at least about 15.

9. The method of claim 7 in which the solvent is free of hydroxyl functional groups.

10. The method of claim 7 in which the solvent is a compound containing hydroxyl functional groups selected from the group consisting of water and $C_{1-8}$ alcohols.

11. The method of claim 7 in which the solvent is water.

12. The method of claim 1 in which the monomers forming the fluorinated polymeric acid further comprise additional comonomers.

13. The method of claim 12 in which the additional comonomers are selected from the group consisting of tetrafluoroethylene, trifluoroethylene, chlorotrifluoroethylene, vinyl fluoride and vinylidene fluoride.

14. The method of claim 2 which comprises converting sulfonyl fluoride of repeating units formed by the fluorinated vinyl ether monomer to an acid form of the following formula

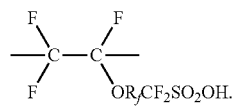

15. The method of claim 3 in which the sum of m plus n is 1.0.

* * * * *